(12) United States Patent
Shin et al.

(10) Patent No.: US 7,638,458 B2
(45) Date of Patent: Dec. 29, 2009

(54) COMPLEX METAL OXIDE CATALYST WITH HIGH (METH) ACRYLIC ACID SELECTIVITY

(75) Inventors: Hyun Jong Shin, Gwangju (KR); Byung Yul Choi, Naju-si (KR); Yeon Shick Yoo, Goyang-si (KR); Young Hyun Choe, Naju-si (KR); Young Jin Cho, Naju-si (KR); Duk Ki Kim, Gwangju (KR); Kwang Ho Park, Daejeon (KR); Joo Yeon Park, Gwangju (KR)

(73) Assignee: LG Chem, Ltd. (KR)

( * ) Notice: Subject to any disclaimer, the term of this patent is extended or adjusted under 35 U.S.C. 154(b) by 101 days.

(21) Appl. No.: 11/502,027

(22) Filed: Aug. 10, 2006

(65) Prior Publication Data

US 2007/0038004 A1 Feb. 15, 2007

(30) Foreign Application Priority Data

Aug. 10, 2005 (KR) ...................... 10-2005-0073402

(51) Int. Cl.
*B01J 27/057* (2006.01)
(52) U.S. Cl. ..................................... 502/215
(58) Field of Classification Search ........................ None
See application file for complete search history.

(56) References Cited

U.S. PATENT DOCUMENTS

| | | | | |
|---|---|---|---|---|
| 3,879,453 A * | 4/1975 | Ono et al. | ................... | 562/547 |
| 4,049,577 A * | 9/1977 | Childress et al. | ............ | 502/178 |
| 4,171,328 A * | 10/1979 | Umemura et al. | ........... | 568/479 |
| 4,186,152 A * | 1/1980 | Yamamoto et al. | .......... | 568/477 |
| 4,217,309 A * | 8/1980 | Umemura et al. | ........... | 568/477 |
| 4,652,673 A * | 3/1987 | Matsumoto et al. | ......... | 562/535 |
| 4,668,653 A * | 5/1987 | Teller et al. | ................. | 502/215 |
| 5,132,269 A * | 7/1992 | Sasaki et al. | ................. | 502/205 |
| 5,134,105 A * | 7/1992 | Paparizos et al. | ............ | 502/205 |
| 5,183,793 A * | 2/1993 | Paparizos et al. | ............ | 502/338 |
| 5,191,116 A * | 3/1993 | Yamamatsu et al. | ......... | 562/549 |
| 5,235,088 A * | 8/1993 | Paparizos et al. | ............ | 558/324 |
| 5,498,588 A * | 3/1996 | Brazdil et al. | ................ | 502/353 |
| 5,821,192 A * | 10/1998 | Seely et al. | .................. | 502/353 |
| 6,383,978 B1 | 5/2002 | Bogan, Jr. | | |
| 6,514,901 B1 | 2/2003 | Lin et al. | | |
| 6,518,216 B1 * | 2/2003 | Han et al. | ................... | 502/215 |
| 6,610,629 B2 * | 8/2003 | Hinago et al. | ................ | 502/300 |
| 6,646,158 B1 | 11/2003 | Karim et al. | | |
| 6,797,840 B2 | 9/2004 | Chaturvedi et al. | | |
| 6,809,219 B2 * | 10/2004 | Han et al. | .................... | 562/549 |
| 6,812,366 B2 * | 11/2004 | Lin | ............................ | 568/470 |
| 6,946,422 B2 * | 9/2005 | Stevenson et al. | ........... | 502/311 |
| 6,998,505 B2 * | 2/2006 | Yada et al. | ................... | 562/545 |
| 7,015,355 B2 * | 3/2006 | Zeyss et al. | ................. | 562/548 |
| 7,049,466 B2 * | 5/2006 | Bogan et al. | ................ | 562/549 |
| 7,319,179 B2 * | 1/2008 | Lopez Nieto et al. | ....... | 585/658 |
| 7,371,883 B2 * | 5/2008 | Fushimi et al. | ............. | 558/323 |
| 2005/0065372 A1 | 3/2005 | Borgmeier et al. | | |
| 2006/0047137 A1 * | 3/2006 | Tu et al. | ..................... | 558/338 |

FOREIGN PATENT DOCUMENTS

| | | | |
|---|---|---|---|
| JP | 51100005 A | * | 9/1976 |
| JP | 05-293389 | | 11/1993 |
| JP | 07144132 A | * | 6/1995 |
| JP | 08-003093 | | 1/1996 |
| JP | 09-176102 | | 7/1997 |
| JP | 10017523 A | * | 1/1998 |
| JP | 2000237592 A | * | 5/2000 |
| JP | 2000237592 A | * | 9/2000 |
| JP | 2001199924 A | * | 7/2001 |
| KR | 10-2002-0082736 | | 10/2002 |
| KR | 2004009755 A | * | 1/2004 |
| KR | 10-2005-0067069 | | 6/2005 |
| WO | 97/46506 | | 12/1997 |

OTHER PUBLICATIONS

International Search Report for International Application No. PCT/KR2006/003138; International Filing Date Aug. 10, 2006; Date of Mailing Nov. 24, 2006.

* cited by examiner

*Primary Examiner*—Brian J Davis
(74) *Attorney, Agent, or Firm*—Cantor Colburn LLP

(57) ABSTRACT

Disclosed are a Mo—Bi—Nb—Te based composite metal oxide; and a process for producing (meth)acrylic acid from at least one reaction material selected from the group consisting of propylene, propane, isobutylene, t-butyl alcohol and methyl-t-butyl ether, wherein the Mo—Bi—Nb—Te based composite metal oxide is used as a catalyst. Also, disclosed is a process for producing (meth)acrylic acid comprising a first step of producing (meth)acrolein as a main product from at least one reaction material selected from the group consisting of propylene, propane, isobutylene, t-butyl alcohol and methyl-t-butyl ether, and a second step of producing (meth) acrylic acid from the (meth)acrolein, wherein yield of (meth) acrylic acid in the product of the first step is 20 mole % or higher.

2 Claims, No Drawings

COMPLEX METAL OXIDE CATALYST WITH HIGH (METH) ACRYLIC ACID SELECTIVITY

This application claims the benefit of the filing date of Korean Patent Application No. 2005-73402, filed on Aug. 10, 2005, in the Korean Intellectual Property Office, the disclosure of which is incorporated herein in its entirety by reference.

TECHNICAL FIELD

The present invention relates to a Mo—Bi—Nb—Te based composite metal oxide, and a process for producing (meth) acrylic acid from propylene or the like by using the Mo—Bi—Nb—Te based composite metal oxide as a catalyst. Also, the present invention relates to a process for producing (meth)acrylic acid comprising a first step of producing (meth) acrolein as a main product from propylene or the like, and a second step of producing (meth)acrylic acid from the (meth) acrolein, wherein the yield of (meth)acrylic acid in the product of the first step is 20 mole % or higher.

BACKGROUND ART

A process for producing an unsaturated fatty acid from an olefin by way of an unsaturated aldehyde is a typical process of catalytic vapor phase oxidation. To perform partial oxidation of olefins, composite oxides containing molybdenum and bismuth, molybdenum and vanadium, or mixtures thereof are used as catalysts. Particular examples of such catalytic vapor phase oxidation include a process of producing (meth)acrylic acid by the oxidation of propylene or isobutylene by way of (meth)acrolein, a process of producing phthalic anhydride by the oxidation of naphthalene or orthoxylene, and a process of producing maleic anhydride by the partial oxidation of benzene, butylene or butadiene.

Generally, (meth)acrylic acid, a final product, is produced from at least one reaction material selected from the group consisting of propylene, propane, isobutylene, t-butyl alcohol or methyl-t-butyl ether (referred to as 'propylene or the like', hereinafter) by a two-step process of vapor phase catalytic partial oxidation. More particularly, in the first step, propylene or the like is oxidized by oxygen, inert gas for dilution, water steam and a certain amount of a catalyst, so as to produce (meth)acrolein as a main product. Then, in the second step, the (meth)acrolein is oxidized by oxygen, inert gas for dilution, water steam and a certain amount of a catalyst, so as to produce (meth)acrylic acid. The catalyst used in the first step is a Mo—Bi-based multinary metal oxide, which oxidizes propylene or the like to produce (meth)acrolein as a main product. Also, some acrolein is continuously oxidized on the same catalyst to partially produce (meth)acrylic acid. The catalyst used in the second step is a Mo—V-based multinary metal oxide, which mainly oxidizes (meth)acrolein in the mixed gas containing the (meth)acrolein produced from the first step to produce (meth)acrylic acid as a main product.

A reactor for performing the aforementioned process is provided either in such a manner that both the two-steps can be performed in one system, or in such a manner that the two steps can be performed in different systems.

As mentioned hereinbefore, the first-step catalyst involved in vapor phase partial oxidation using propylene or the like as a starting material is a multinary metal oxide, with which (meth)acrolein is produced as a main product and at most 10% of (meth)acrylic acid is produced.

As disclosed in Japanese Laid-Open Patent No. Hei8-3093, a conventional first-step catalyst is a composite oxide represented by the formula of $Mo_a$—$Bi_b$—$Fe_c$—$A_d$—$B_e$—$C_f$—$D_g$—$O_x$, wherein Mo, Bi and Fe represent molybdenum, bismuth and iron, respectively; A is nickel and/or cobalt; B is at least one element selected from the group consisting of manganese, zinc, calcium, magnesium, tin and lead; C is at least one element selected from the group consisting of phosphorus, boron, arsenic, Group 6B elements in the Periodic Table, tungsten, antimony and silicon; D is at least one element selected from the group consisting of potassium, rubidium, cesium and thallium; each of a, b, c, e, f and g is a number satisfying the conditions of $0<b\leq10$, $0<c\leq10$, $1\leq d\leq 10$, $0\leq e\leq 10$, $0\leq f\leq 20$, and $0<g\leq 2$, when $a=12$; and x is a value defined by the oxidation state of each element. When vapor phase catalytic oxidation of propylene is performed with molecular oxygen by using the above first-step catalyst and by operating the first-step catalyst layer at a temperature of 325° C., acrolein is produced with a yield of 81.3% and acrylic acid is produced with a yield of 11%. In other words, acrylic acid content is low in the reaction product obtained by using the first-step catalyst.

Meanwhile, Japanese Laid-Open Patent No. Hei5-293389 discloses a catalyst represented by the formula of $Mo_aBi_bF-e_cA_dX_eY_fZ_gSi_hO_i$, wherein Mo, Bi, Fe, Si and O represent molybdenum, bismuth, iron, silicon and oxygen, respectively; A is at least one element selected from the group consisting of cobalt and nickel; X is at least one element selected from the group consisting of magnesium, zinc, manganese, calcium, chrome, niobium, silver, barium, tin, tantalum and lead; Y is at least one element selected from the group consisting of phosphorus, boron, sulfur, selenium, Group 6B elements in the Periodic Table, cerium, tungsten, antimony and titanium; Z is at least one element selected from the group consisting of lithium, sodium, potassium, rubidium, cesium and thallium; and each of a, b, c, d, e, f, g, h and i represents the atomic ratio of each element, with the proviso that when $a=12$, $b=0.01\sim3$, $c=0.01\sim5$, $d=1\sim12$, $e=0\sim6$, $f=0\sim5$, $g=0.001\sim1$, $h=0\sim20$, and i is the oxygen atom number needed to satisfy the atomic valence of each element. When vapor phase catalytic oxidation of propylene is performed by using the above first-step catalyst to produce acrolein and acrylic acid, acrylic acid is produced with a yield of 6.2 mole % under a propylene conversion ratio of 99.1 mole % and an acrolein selectivity of 89.6 mole %. In other words, acrylic acid content is still low in the reaction product obtained by using the first-step catalyst.

In a process for producing (meth)acrylic acid, the temperature of the second-step catalyst layer varies depending on the selectivity of (meth)acrolein and (meth)acrylic acid (i.e. the first-step catalytic reaction product) and the amount of (meth) acrolein unreacted in the second-step catalytic reaction. The second-step catalyst layer is operated in such a manner that unreacted (meth)acrolein can be minimized. When (meth) acrolein selectivity is high in the first-step catalytic reaction product, the second-step catalyst layer is subjected to an increased load and concentration, resulting in an increase in reaction temperature and degradation of the lifetime of the catalyst. Additionally, when a concentration of unreacted (meth)acrolein is increased due to the degradation in catalytic activity, a waste gas incineration system (WGIS) may be overloaded, resulting in degradation of the lifetime of a waste gas treating catalyst.

DISCLOSURE OF THE INVENTION

Therefore, the present invention has been made in view of the above-mentioned problems. The inventors of the present invention have found that when a Mo—Bi—Nb—Te based composite metal oxide is used as the first-step catalyst in the production of (meth)acrylic acid from propylene or the like, yield and/or selectivity of (meth)acrylic acid increases in the first-step reaction product, and thus (meth)acrolein load and concentration decrease in the second-step to such a degree that (meth)acrolein conversion ratio can reach 100%. The present invention is based on this finding.

According to an aspect of the present invention, there is provided a Mo—Bi—Nb—Te based composite metal oxide.

According to another aspect of the present invention, there is provided a process for producing (meth)acrylic acid from at least one reaction material selected from the group consisting of propylene, propane, isobutylene, t-butyl alcohol and methyl-t-butyl ether by using a Mo—Bi—Nb—Te based composite metal oxide as a catalyst.

According to still another aspect of the present invention, there is provided a process for producing (meth)acrylic acid comprising a first step of producing (meth)acrolein as a main product from at least one reaction material selected from the group consisting of propylene, propane, isobutylene, t-butyl alcohol and methyl-t-butyl ether, and a second step of producing (meth)acrylic acid from the (meth)acrolein, wherein yield of (meth)acrylic acid in the product of the first step is 20 mole % or higher.

Hereinafter, the present invention will be explained in more detail.

Mo—Bi-based first-step metal oxide catalysts for producing (meth)acrolein from propylene or the like, which have been disclosed to date, generally provide a conversion ratio (selectivity) from propylene or the like to (meth)acrolein and (meth)acrylic acid of about 90% or more, wherein the molar ratio of (meth)acrolein to (meth)acrylic acid in the first-step reaction product is about 9:1. Additionally, when the first-step reaction product is subjected to the second-step reaction, it is possible to obtain a (meth)acrolein conversion ratio of about 98%.

The inventors of the present invention have found that when a Mo—Bi-based composite oxide also containing both Nb and Te, i.e. a Mo—Bi—Nb—Te based composite metal oxide is prepared and used as the first-step reaction catalyst, it is possible to obtain a conversion ratio (selectivity) of (meth)acrolein and (meth)acrylic acid from propylene or the like of 90% or more, as well as a molar ratio of (meth)acrolein to (meth)acrylic acid in the first-step reaction product of approximately 8:2~7:3.

Additionally, the inventors of the present invention have found that use of a Mo—Bi—Nb—Te based composite metal oxide as the first-step catalyst provides a decreased selectivity of (meth)acrolein in the first-step reaction product and an increased selectivity of (meth)acrylic acid as mentioned above, and thus the second-step reaction is subjected to a decreased load and concentration of (meth)acrolein as a reactant, so that the second-step reaction can provide a (meth)acrolein conversion ratio of 100% after the completion of the reaction.

Further, according to the present invention, since selectivity of (meth)acrylic acid increases from (meth)acrolein and (meth)acrylic acid, which are the main reaction products that have passed through the first-step catalyst, complete conversion of (meth)acrolein can be accomplished in the subsequent second-step catalytic reaction step. Hence, it is possible to operate the overall process under a high load and concentration so as to provide a high yield, and to improve the lifetime of the second-step catalyst.

In brief, the present invention is based on the fact that a Mo—Bi—Nb—Te based composite metal oxide, used as the first-step reaction catalyst in a process for producing (meth)acrylic acid from propylene or the like, provides a lower (meth)acrolein selectivity and a higher (meth)acrylic acid selectivity in the first-step reaction product, when compared to other conventional Mo—Bi metal oxides currently used as the first-step catalyst.

(1) Preferably, the Mo—Bi—Nb—Te based composite metal oxide according to the present invention is a composite metal oxide represented by the following Formula 1:

$$Mo_aBi_bNb_cTe_dA_eB_fC_gD_hE_iF_jO_k$$ [Formula 1]

Wherein Mo represents molybdenum, Bi represents bismuth, Nb represents niobium, and Te represents tellurium;

A is at least one element selected from the group consisting of W, Sb, As, P, Sn and Pb;

B is at least one element selected from the group consisting of Fe, Zn, Cr, Mn, Cu, Ru, Pd, Ag and Ru;

C is at least one element selected from the group consisting of Co, Cd, Ta, Pt and Ni;

D is at least one element selected from the group consisting of Si, Al, Zr, V and Ce;

E is at least one element selected from the group consisting of Se, Ga, Ti, Ge, Rh and Au;

F is at least one element selected from the group consisting of Na, K, Li, Rb, Cs, Ca, Mg, Sr, Ba and MgO;

each of a, b, c, d, e, f, g, h, i, j and k represents the atomic ratio of each element;

wherein when a=12, b is 0.01~20, c is 0.001~20, d is 0.001~20, e is 0~15, f is 0~20, g is 0~20, h is 0~10, is 0~10, j is 0~10, and k is a number defined by the oxidation state of each of the above elements.

When used as a catalyst, the Mo—Bi—Nb—Te based composite metal oxide according to the present invention may be used alone or may be supported on an inert carrier. Particular examples of the carrier that may be used in the present invention include porous or non-porous alumina, silica-alumina, silicon carbide, titanium dioxide, magnesium oxide, aluminum sponge, or the like. Additionally, the carrier may take a cylindrical shape, a hollow cylindrical shape or a spherical shape, but is not limited thereto. For example, a catalyst having a cylindrical shape preferably has a ratio of length to diameter (outer diameter) (L/D ratio) of 1~1.3, and more preferably has a L/D ratio of 1. A catalyst having a cylindrical or spherical shape preferably has an outer diameter of 3~10 mm, more preferably of 5~8 mm.

The Mo—Bi—Nb—Te based composite metal oxide according to the present invention may be prepared by a conventional method for producing a composite metal oxide, except that a different composition of elements is used.

There is no particular limitation in the shape of a metal precursor forming the Mo—Bi—Nb—Te based composite metal oxide. For example, a compound that is provided originally in the form of an oxide or can be converted into an oxide by heating (i.e. calcination) at least in the presence of oxygen, for example, halogenide, nitride, formate, oxalate, citrate, acetate, carbonate, amine complex, ammonium salt and/or hydroxide may be used as a starting material.

According to an embodiment of the present invention, the method for preparing the composite metal oxide comprises the steps of: dissolving or dispersing a predetermined amount (stoichiometric amount) of each starting material containing each element forming the composite metal oxide into an aqueous medium; heating the resultant solution or dispersion while stirring it; allowing the system to evaporate to obtain a dry solid and drying and pulverizing the solid; and molding the powder into a desired shape via extrusion molding to obtain tablets or granules. In this case, glass fibers and inorganic fibers including various kinds of whiskers, which are known to improve the strength and frictional resistance, may be further added. Additionally, in order to control the properties of the catalyst and to obtain excellent reproducibility, other additives known as powder binders, such as ammonium nitrate, cellulose, starch, polyvinyl alcohol, stearic acid, or the like, may be used.

The composite metal oxide catalyst according to the present invention may be obtained by calcining the molded product obtained as described above or the same product supported on a carrier under a flow of 0.2~2 m/s at 300~600° C. for about 1~10 hours. The calcination step may be performed under an inert gas atmosphere, an oxidative atmosphere, for example, air (a mixture of inert gas and oxygen), or a reductive atmosphere (e.g., a mixture of inert gas, oxygen and $NH_3$, CO and/or $H_2$). The calcination step may be performed for a period of several minutes to several hours, and the calcination period generally decreases as the temperature increases.

(2) The Mo—Bi—Nb—Te based composite metal oxide according to the present invention may be used as a catalyst to produce (meth)acrylic acid from at least one reactant selected from the group consisting of propylene, propane, isobutylene, t-butyl alcohol, and metyl-t-butyl ether. In this case, conversion (selectivity) from propylene or the like into (meth)acrolein and (meth)acrylic acid may be accomplished at a ratio of 90% or more, and the molar ratio of (meth)acrolein:(meth) acrylic acid in the reaction product is approximately 8:2~7:3.

Particularly, the Mo—Bi—Nb—Te based composite metal oxide according to the present invention may be used as a catalyst for the first-step partial oxidation in a process for producing (meth)acrylic acid from a reaction material such as propylene or the like, the process comprising a first step for producing (meth)acrolein as a main product from the reactants such as propylene or the like and a second step for producing (meth)acrylic acid from the (meth)acrolein.

When vapor phase catalytic oxidation is carried out by using the Mo—Bi—Nb—Te based composite metal oxide according to the present invention as a catalyst, there is no particular limitation in systems and operation conditions thereof used in the process. Reactors that may be used in the present invention include conventional fixed-bed, fluidized-bed and moving-bed reactors. For example, the process for producing (meth)acrylic acid may be performed in a shell-and-tube reactor and the Mo—Bi—Nb—Te based composite metal oxide according to the present invention may be packed in a reaction tube so as to be used as a first-step fixed bed catalyst. Herein, as a second-step catalyst, Mo—V-based multinary metal oxide may be used to oxidize (meth)acrolein-containing mixed product gas generated by the first-step Mo—Bi—Nb—Te based composite metal oxide catalyst, thereby producing (meth)acrylic acid.

To perform the reaction, reaction conditions, which are generally adopted for producing (meth)acrylic acid and (meth)acrolein from a reaction material such as propylene or the like via vapor phase catalytic oxidation, may be used. For example, a gas mixture as a starting material, which contains 7 vol % or more of reactants such as propylene or the like, 10~13 vol % of molecular oxygen and 60~80 vol % of inert gas functioning as a diluent (e.g. nitrogen, carbon dioxide, steam, or the like), is caused to be in contact with the catalyst according to the present invention, at a temperature of 250~500° C. under a pressure of 0.1~3 kg/cm²G with a space velocity of 300~5000 $hr^{-1}$ (STP) to carry out a desired reaction.

The second-step catalytic reaction is suitably carried out at a reaction temperature of 200~450° C., preferably of 265~370° C., under a reaction pressure of 0.1~10 atm, preferably of 0.5~3 atm. For example, a feed gas as reactants, which contains 4~10 vol % of (meth)acrolein, 10~13 vol % of oxygen, 5~60 vol % of water steam and 20~80 vol % of inert gas, is introduced onto the catalyst with a space velocity of 500~5000 $hr^{-1}$ (STP) to perform oxidation.

(3) Further, the present invention provides a process for producing (meth)acrylic acid comprising a first step of producing (meth)acrolein as a main product from propylene or the like, and a second step of producing (meth)acrylic acid from the (meth)acrolein, wherein yield of (meth)acrylic acid in the product of the first step is 20 mole % or higher.

The yield as high as 20 mol % of (meth)acrylic acid in the first-step reaction product can be accomplished by using the Mo—Bi—Nb—Te based composite metal oxide according to the present invention as the first-step catalyst.

Meanwhile, when (meth)acrylic acid is produced with a yield of 20 mole % or higher in the first-step reaction product, it is possible to obtain a conversion ratio of (meth)acrolein of 98~100%, preferably 100%, in the second-step reaction. Herein, the (meth)acrolein conversion ratio as high as 98~100% also depends on the content of propylene or the like in the reaction mixture introduced to the first-step. Preferably, propylene or the like is contained in the reaction mixture gas introduced into the first-step reaction in an amount of 7~10 vol % in order to accomplish a (meth)acrolein conversion ratio of 100%.

MODE FOR CARRYING OUT THE INVENTION

Reference will now be made in detail to the preferred embodiments of the present invention. It is to be understood that the following examples and comparative examples are illustrative only, and the scope of the present invention is not limited thereto.

Preparation of First-Step Reaction Catalyst

Preparation Example 1

Catalyst 1

First, 2500 ml of distilled water was heated and stirred at 70° C.~85° C. and 1000 g of ammonium molybdate was added thereto to form solution (1). Next, 274 g of bismuth nitrate, 228 g of ferrous nitrate and 2.3 g of potassium nitrate were added to 400 ml of distilled water, the materials were mixed thoroughly, 71 g of nitric acid was added thereto, and the materials were dissolved sufficiently to form solution (2). To 200 ml of distilled water, 686 g of cobalt nitrate was dissolved to form solution (3). After mixing solution (2) with solution (3), the mixed solution was further mixed with solution (1) while maintaining the temperature at 40~60° C. to provide a catalyst suspension.

The catalyst suspension was dried to produce $Mo_{12}Bi_{1.2}Fe_{1.2}Co_5K_{0.05}$ and the catalyst was pulverized into a size of 150 μm or less. The resultant catalyst powder was mixed for 2 hours and formed into a cylindrical shape. The catalyst was formed to have an outer diameter of 4.0~8.0 mm, and calcined at 500° C. for 5 hours under the air, and then the catalytic activity was verified.

Preparation Example 2

Catalyst 2

Catalyst 2 was provided in the same manner as described in Preparation Example 1, except that 63 g of niobium chloride and 150 g of tellurium chloride were further added to form solution (1). The catalyst had the elemental composition of $Mo_{12}Nb_{0.5}Te_1Bi_{1.2}Fe_{1.2}Co_5K_{0.05}$ except oxygen.

Preparation Example 3

Catalyst 3

Catalyst 3 was provided in the same manner as described in Preparation Example 1, except that 127 g of niobium chloride and 150 g of tellurium nitrate were further added to form solution (1). The catalyst had the elemental composition of $Mo_{12}Nb_{1.0}Te_{1.0}Bi_{1.2}Fe_{1.2}Co_{4.5}K_{0.05}$ except oxygen.

Preparation Example 4

Catalyst 4

Catalyst 4 was provided in the same manner as described in Preparation Example 1, except that 63 g of niobium chloride and 75 g of tellurium chloride were further added to form solution (1). The catalyst had the elemental composition of $Mo_{12}Nb_{0.5}Te_1Bi_{1.2}Fe_{1.2}Co_{4.5}K_{0.05}$ except oxygen.

Preparation Example 5

Catalyst 5

First, 2000 ml of distilled water was heated and stirred at 100° C. and 246 g of ammonium tungstate, 1000 g of ammonium molybdate and 220 g of ammonium vanadate were dissolved therein to form solution (1). Next, 228 g of copper nitrate and 49 g of strontium nitrate were added to 500 ml of distilled water, and the materials were mixed thoroughly to form solution (2). Solution (1) was mixed with solution (2) to provide a suspension. The suspension was treated by using a homogenizer for at least 30 minutes and was coated on spherical carriers having an outer diameter of 4.0~8.0 mm by using a spray nozzle to an amount of 20~30 wt % as expressed by the catalytically active component present in the suspension. The coated catalyst was dried at 120° C. sufficiently and calcined at 400° C. for at least 5 hours to provide spherical catalyst particles having a final outer diameter of 5 mm (±0.2).

The catalyst had the elemental composition of $Mo_{12}W_{2.0}V_{4.0}Cu_{2.0}Sr_{0.5}$ except oxygen.

EXPERIMENT

Catalyst Packing and Catalytic Activity Test

To a 3 m stainless steel reactor having an inner diameter of 1 inch and heated with molten nitrate salt, alumina silica was packed to a height of 150 mm as an inert material, and any one of Catalysts 1~4 was packed to a height of 2800 mm as the first-step catalyst, from the inlet of the reaction gas toward the outlet.

Then, alumina silica was packed to a height of 150 mm as an inert material and Catalyst 5 was packed to a height of 2900 mm as the second-step catalyst. Propylene was subjected to vapor phase oxidation by using the reactor to produce acrolein and acrylic acid. The first-step oxidation was performed by introducing feed gas containing 7 vol % of propylene, 13 vol % of molecular oxygen, 8 vol % of water steam and 72 vol % of inert gas onto the catalyst with a space velocity of 1500 hr$^{-1}$ (STP), at a reaction temperature of 320° C., under a reaction pressure of 0.7 atm. The second-step oxidation was performed at a reaction temperature of 276° C., under a reaction pressure of 0.1~3 kg/cm$^2$G.

In the following Tables 1 and 2, conversion ratio of a reaction material, selectivity and yield are calculated based on the following Mathematical Formulae 1~7.

first-step propylene conversion ratio(%)=[moles of reacted propylene/moles of supplied propylene]× 100       [Mathematical Formula 1]

yield(%)of acrolein in the first step=[moles of produced acrolein/moles of supplied propylene]× 100       [Mathematical Formula 2]

yield(%)of acrylic acid in the first step=[moles of produced acrylic acid/moles of supplied propylene]× 100       [Mathematical Formula 3]

selectivity(%)of acrolein+acrylic acid in the first step= [moles of produced acrolein and acrylic acid/ moles of reacted propylene]×100       [Mathematical Formula 4]

second-step acrolein conversion ratio(%)=[moles of reacted acrolein/moles of supplied acrolein]×100       [Mathematical formula 5]

yield(%)of acrylic acid in the second step=[moles of produced acrylic acid/moles of supplied acrolein]×100       [Mathematical Formula 6]

selectivity(%)of acrylic acid in the second step= [moles of produced acrylic acid/moles of reacted acarolein]×100       [Mathematical Formula 7]

The experimental results of the Examples according to the present invention and Comparative Example are shown in the following Table 1 (first-step oxidation) and Table 2 (second-step oxidation).

TABLE 1

| Item | Propylene conversion(%) 320° C. | Acrolein yield (mole %) | Acrylic acid yield (*1) (mole %) | Acrylic acid + acrolein selectivity (%) |
|---|---|---|---|---|
| Comp. Ex. 1 (Catalyst 1) | 97.01 | 80.21 | 9.31 | 92.27 |
| Ex. 1 (Catalyst 2) | 97.21 | 65.34 | 25.56 | 93.50 |
| Ex. 2 (Catalyst 3) | 97.60 | 66.12 | 26.14 | 95.05 |
| Ex. 3 (Catalyst 4) | 98.01 | 66.04 | 26.19 | 94.10 |

TABLE 2

| Item | Acrolein conversion (mole %) Reaction temperature 276° C. | Acrylic acid yield (*2) (mole %) | Acrylic acid selectivity (mole %) |
|---|---|---|---|
| Comp. Ex. 1 (Catalyst 1 + Catalyst 5) | 98.14 | 87.12 | 88.77 |
| Ex. 1 (Catalyst 2 + Catalyst 5) | 100 | 90.90 | 90.90 |
| Ex. 2 (Catalyst 3 + Catalyst 5) | 100 | 92.26 | 92.26 |
| Ex. 3 (Catalyst 4 + Catalyst 5) | 100 | 92.23 | 92.23 |

INDUSTRIAL APPLICABILITY

As can be seen from the foregoing, when the Mo—Bi—Nb—Te based composite metal oxide according to the present invention is used as the first-step catalyst in the production of (meth)acrylic acid from propylene or the like, yield and/or selectivity of (meth)acrylic acid increases in the first-step reaction product, and thus (meth)acrolein load decreases in the second-step to such a degree that (meth)acrolein conversion ratio can reach 98~100%.

While this invention has been described in connection with what is presently considered to be the most practical and preferred embodiment, it is to be understood that the invention is not limited to the disclosed embodiment and the drawings. On the contrary, it is intended to cover various modifications and variations within the spirit and scope of the appended claims.

The invention claimed is:

1. A Mo—Bi—Nb—Te based composite metal oxide, which is represented by the following Formula 1:

$$Mo_a Bi_b Nb_c Te_d A_e B_f C_g D_h E_i F_j O_k \quad \text{[Formula 1]}$$

wherein Mo represents molybdenum, Bi represents bismuth, Nb represents niobium, and Te represents tellurium;

A is at least one element selected from the group consisting of W, Sb, As, P, Sn and Pb;

B is at least one element selected from the group consisting of Fe, Zn, Cr, Mn, Cu, Pd, Ag and Ru;

C is at least one element selected from the group consisting of Co, Cd, Ta, Pt and Ni;

D is at least one element selected from the group consisting of Si, Al, Zr, and Ce;

E is at least one element selected from the group consisting of Se, Ga, Ti, Ge, Rh and Au;

F is at least one element selected from the group consisting of Na, K, Li, Rb, Ca, Sr, and Ba;

each of a, b, c, d, e, f, g, h, i, j and k represents the atomic ratio of each element;

wherein when a=12, b is 0.01~20, c is 0.001~20, d is 0.001~20, e is 0~15, f is 0~20, g is 0~20, h is 0~10, i is 0~10, j is 0~10, and k is a number defined by the oxidation state of each of the above elements.

2. A catalyst comprising the Mo—Bi—Nb—Te based composite metal oxide according to claim 1.

* * * * *